(12) United States Patent
Jordan

(10) Patent No.: US 9,101,356 B1
(45) Date of Patent: Aug. 11, 2015

(54) STEERABLE SUTURE INSTRUMENT

(71) Applicant: Christopher S. Jordan, Midwest City, OK (US)

(72) Inventor: Christopher S. Jordan, Midwest City, OK (US)

(*) Notice: Subject to any disclaimer, the term of this patent is extended or adjusted under 35 U.S.C. 154(b) by 231 days.

(21) Appl. No.: 13/987,500

(22) Filed: Jul. 31, 2013

(51) Int. Cl.
*A61B 17/04* (2006.01)

(52) U.S. Cl.
CPC .................................. *A61B 17/0469* (2013.01)

(58) Field of Classification Search
CPC ................... A61B 18/1492; A61B 2017/003; A61M 25/0147; A61M 25/0138; A61M 25/0133
USPC .......................................... 606/139, 144–146
See application file for complete search history.

(56) References Cited

U.S. PATENT DOCUMENTS

| | | |
|---|---|---|
| 4,441,497 A | 4/1984 | Paudler |
| 4,719,924 A | 1/1988 | Crittenden |
| 4,874,376 A | 10/1989 | Hawkins, Jr. |
| 5,011,473 A | 4/1991 | Gatturna |
| 5,195,968 A | 3/1993 | Lundquist |
| 5,318,528 A | 6/1994 | Heaven |
| 5,350,391 A | 9/1994 | Lacovelli |
| 5,501,654 A | 3/1996 | Failla |
| 6,464,711 B1 | 10/2002 | Emans |
| 6,530,913 B1 | 3/2003 | Giba |
| 7,381,205 B2 | 6/2008 | Thommen |
| 8,376,990 B2 | 2/2013 | Ponzi |
| 8,475,436 B1 * | 7/2013 | Jordan .............................. 606/1 |
| 2005/0277874 A1 * | 12/2005 | Selkee ....................... 604/95.04 |
| 2006/0079911 A1 | 4/2006 | Muramatsu |
| 2009/0177219 A1 | 7/2009 | Conlon |
| 2013/0204096 A1 * | 8/2013 | Ku et al. ........................ 600/301 |

* cited by examiner

*Primary Examiner* — Katherine M Shi
(74) *Attorney, Agent, or Firm* — Randal D. Homburg

(57) ABSTRACT

A steerable surgical suture passer providing single hand operation to selectively direct the operation tip in an upward or downward direction to reduce the degree of collateral tissue damage during the use of the instrument, the suture passer providing a shaped handle for ambidextrous use and defining an inner socket, an integrated inner member defining an upper trigger and lower trigger at a proximal end, a pair of resilient intermediate parallel shaft members and a distal operational tip, the inner member pivotally secured within the inner socket by a single pin and a rigid hollow shaft support tube connected to the handle through which the resilient parallel shaft members are directed, allowing the surgeon to steer the operations tip and required when performing a surgical procedure.

5 Claims, 7 Drawing Sheets

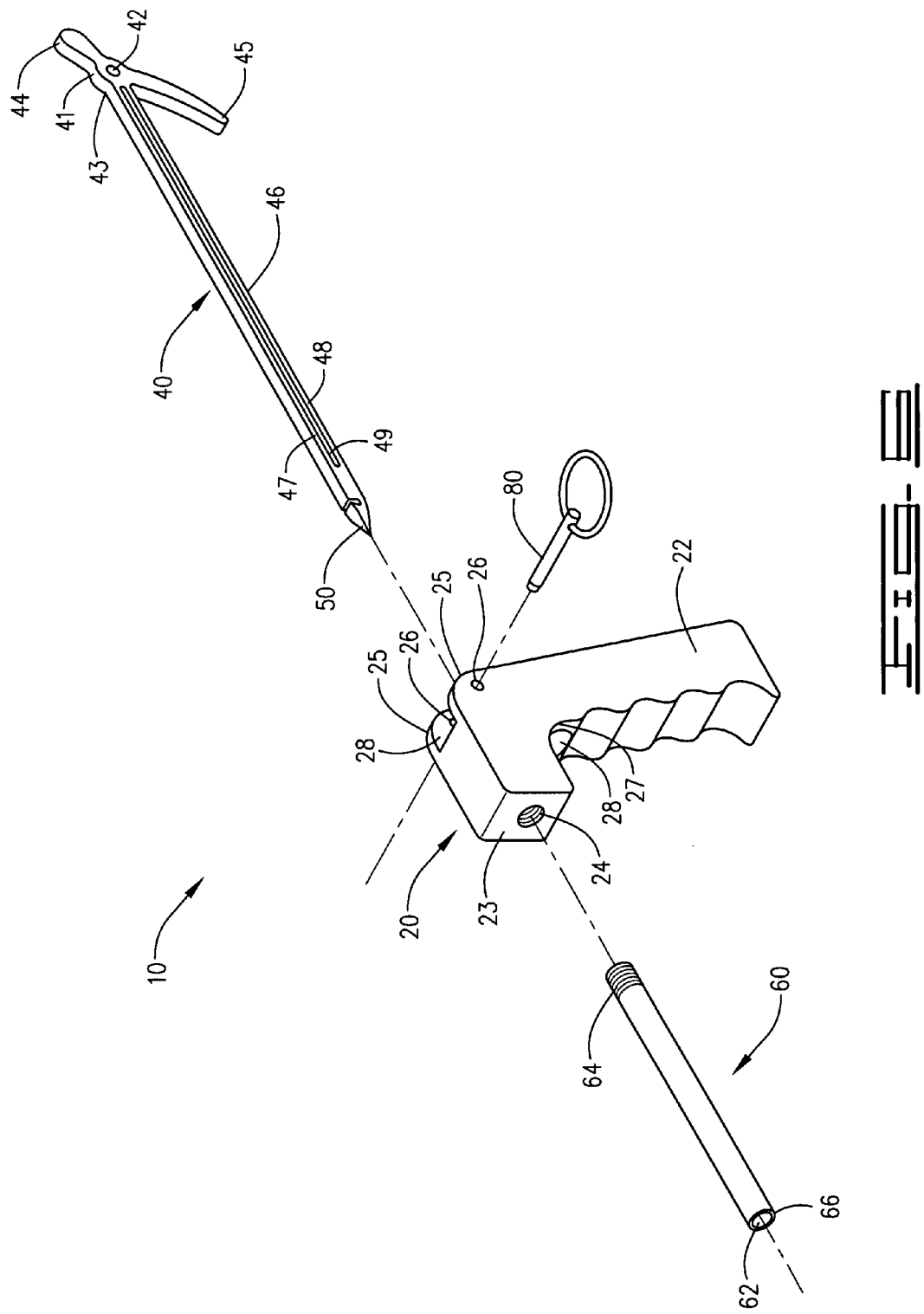

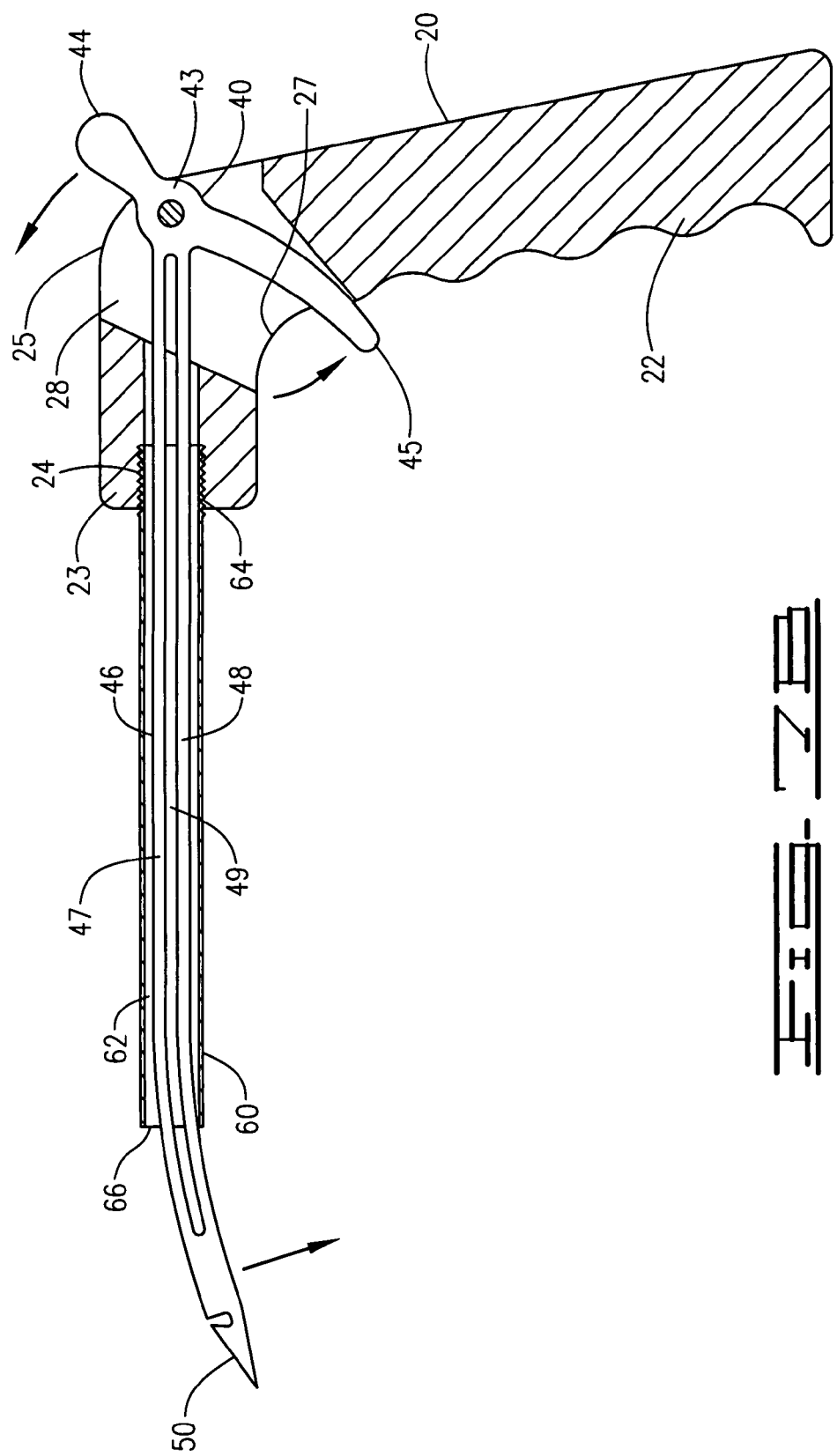

STEERABLE SUTURE INSTRUMENT

CROSS REFERENCE TO RELATED APPLICATIONS

None.

I. BACKGROUND OF THE INVENTION

1. Field of Invention

A steerable surgical suture passer providing single hand operation to selectively direct the operation tip in an upward or downward direction to reduce the degree of collateral tissue damage during the use of the instrument, the suture passer providing a shaped handle for ambidextrous use and defining an inner socket, an integrated inner member defining an upper trigger and lower trigger at a proximal end, a pair of resilient intermediate parallel shaft members and a distal operational tip, the inner member pivotally secured within the inner socket by a single pin and a rigid hollow shaft support tube connected to the handle through which the resilient parallel shaft members are directed, allowing the surgeon to steer the operations tip and required when performing a surgical procedure.

2. Description of Prior Art

The following U.S. patents and publications were discovered and are disclosed within this application for utility patent. All relate to surgical instruments with some of them using a steering mechanism in some form or manner.

Several of the surgical instruments are shown by example, which may be adapted to the presently disclosed technology are provided for a brief reference as to the types of surgical instruments for which the improvements to the art as surgical instruments for sale and use by Inlet Medical Inc., disclosing suture passers, sutures, ligament graspers, tie knot pushers, clamps. Those references have not been included for review due to their having been removed from public access and thus not included by reference. They still have made reference to small surgical instruments to reduce the amount of collateral damage to surrounding tissue caused by their insertion into a surgical site. Other identified surgical instruments are suture punches and penetrating suture graspers. These prior surgical instruments are further identified as the SCORPION™, made by Arthrex of Naples, Fla., and the EXPRESSSEW™, made by Mitek of Raynham, Mass.

The same inventor as in the present application is the inventor of record in U.S. Pat. No. 8,475,436, recently issued. This patent disclosed a prior art bi-directional surgical instrument disclosed a static handle, a base anchor bracket, a trigger mechanism defining a front trigger extension and a rear trigger extension which direct the sliding of a pair of upper and lower resilient members which are attached at a base end to a sedge shaped portion which is attached to the trigger mechanism, each resilient member attached at respective distal ends wherein the trigger mechanism moving in one rotational direction bends the attached distal ends in upwards while the trigger mechanism being moved in the opposing direction bends the attached distal ends downwards. This device serves the same function as the present steerable suture instrument but it requires more component parts in its disclosed embodiment, a more complicated assembly of the disclosed components and a significant greater expense in production of its disclosed embodiment than the present disclosed suture instrument, which only has four primary component parts with a simple single pin assembly.

A steerable catheter, identified in U.S. Pat. No. 8,376,990 to Ponzi, discloses two puller wires connected to compression coils with each of the two wires connected to a tip on a far end and a non-descriptive steering end with the other ends connected to a "bi-directional control handle" referenced by other patents. A very similar device is disclosed within U.S. Pat. No. 5,195,968 to Lundquist, which discloses another steerable catheter. A pair of scissors within a laparoscopic instrument is disclosed in U.S. Pat. No. 5,350,391 to Iacovelli, with one wire operating one of the pairs scissor members and another wire moving the scissor head at a pivot. In U.S. Pat. No. 5,501,654 to Faillia, an endoscope has a bendable end that provides a single spring member that curves in a singular direction when released from the inside of a stiff shaft with a control handle that extends the single spring member and retracts it from the stiff shaft within which it is withdrawn and extended.

U.S. Pat. No. 5,011,473 to Gatturna discloses a device for securing and positioning a wire to a needle, including a probe wire through a cannula needle and more particularly, towards a locking and positioning device for a needle wire localizer. There is a J-curved tip next to the point of the needle. Another similar needle guide is indicated in U.S. Pat. No. 4,874,376 to Hawkins, Jr. An earlier suture passer is shown in U.S. Pat. No. 4,441,497 to Paudler, which has a plurality of elongated flexible members attached at two common ends forming dual piercing tips, with the suture placed between connected flexible members as the device is inserted into a surgical pathway, with the members bending around curves through manual manipulation.

A ligating device is shown in Patent Application Publication No. 2006/0079911 to Muramatsu, which demonstrates an introduction tube inserted into a location within the surgical site with at least two manipulating wires movably inserted within the tube and at least two clips having a proximal end portion with a pinch section at the end of the tube. The wires manipulate the clips within the tube with the clips having the ability to grasp tissue and pull it within the tube. A suture passer with a curved suture carrier with a sharpened tip, shown with two suture passers, allow for the upward insertion of sutures from below and insertion level for passing and directing the sutures upwards through tissue after piercing the tissue from above.

In U.S. Pat. No. 4,719,924 to Crittenden, a steerable guide wire provides the means to adjust the curvature of the tip of a surgical instrument during a cardiovascular surgical procedure. An inner tubular member rotating inside an outer tubular member provides the means for rotation of a surgical instrument, with an arthroscopic grasper mounted on the end of the outer member, disclosed in U.S. Pat. No. 5,318,528 to Heaven. A pull cable inside a catheter inserted into an artery and extended into the heart, specifically during a transmyocardial revascularization procedure, is use to steer the tip of the instrument through the artery, the pull cable at the handle portion of the instrument as disclosed in U.S. Pat. No. 6,530,913 to Giba. In U.S. Pat. No. 7,381,205 to Thommen, a spring elastic guide wire within a tub having a spiral section displaces a distal end of a flexible catheter tube.

None of the above noted patents, nor any others observed by the applicant, demonstrate a shaped handle, an integrated shaped inner member defining an upper trigger and lower trigger and further extending a pair of resilient parallel shaft members terminating into an operational tip, the inner member pivotally secured within the handle by a single pin and a rigid hollow shaft support tube connected to the handle through which the resilient parallel shaft members are directed, the activation of either or both of the two triggers causing the operational end of the surgical instrument to bend in an intended direction and degree, steering the operational end of the surgical instrument through tissue, the instrument being turned to steer the operational end in any intentional direction.

II. SUMMARY OF THE INVENTION

During a surgical procedure, surgical instruments comprising a handle and shaft portion and an application end are used by surgeons. These include cutting tools, suture passers, probes, grasping tools and clamps, among several. The insertion of these instruments is accomplished by either the tool cutting its own pathway, or the tools being inserted through a hole that is already cut through the tissue to the site of the surgical procedure. Quite often, this pathway is not a straight line, having the pathway directed around certain tissues as opposed to through them. This is difficult to accomplish using a rigid and straight instrument. Where the entry is made with a rigid instrument, more extensive damage is done to the surrounding tissue leading to a longer period of recovery and the risk of permanent injury to the surrounding tissues.

In some case, surgical instruments do include a curved portion at or near an end, or at least include an angled application end. However, the pathway of these surgical instruments are restricted to the pathway being cut along the predetermined curved portion. Often tissue is unnecessarily damaged, stretched or displaced along the pathway due to having to insert and remove the surgical instrument to achieve the direction and angle desired to reach the site of the surgery from the external insertion point. It would be more suitable and less damaging to the collateral tissue if the surgeon had the ability to steer the surgical instrument, reducing the destruction of collateral tissue along the pathway, and actually have the ability to direct the surgical instrument at any desired angle or curve and in more than one direction.

It is one of several objectives to provide a surgical instrument having an intentionally directed steerable operational end to reduce the amount of tissue damage during the insertion and use of the surgical instrument and the attached tool. It would also be an objective to provide the surgical instrument with the ability to be steered in tow opposite directions under the direct control of the surgeon, using a single finger or thumb movement during the operation with the same hand used to grasp the instrument, manipulate the degree and direction of the bend of the operational end, and to guide the surgical instrument within the location of surgery intended by the surgeon with a reduction in the amount of damage to any collateral tissue at the surgical site. It is yet another objective to make the instrument in a simple, inexpensive and sanitary conscious manner where the instrument is cheap to manufacture, easy to assembly and easy to clean after use, with the handle, extension tub and pin made of metal with smooth surfaces with little if any obscured areas making them easy to clean, and the shaped inner member made of plastic, nylon or other moldable and resilient material which is cheap enough to provide and manufacture that it can simply be disposed of after use.

III. DESCRIPTION OF THE DRAWINGS

The following drawings are submitted with this utility patent application.

FIG. 6 is an exploded perspective view of the four primary components of the steerable surgical instrument, and as disassembled for the purpose of post-surgical cleaning.

FIG. 7B is the same view as shown in FIG. 4, with the upper thumb trigger pushed forward and/or the lower finger trigger pulled towards the grip portion of the handle, rotating the hub counter clockwise and further thrusting the upper tension strut forward towards the operational end and drawing the lower tension strut towards the trigger causing the operational tip to be diverted downward.

IV. DESCRIPTION OF THE PREFERRED EMBODIMENT

Figure 1:
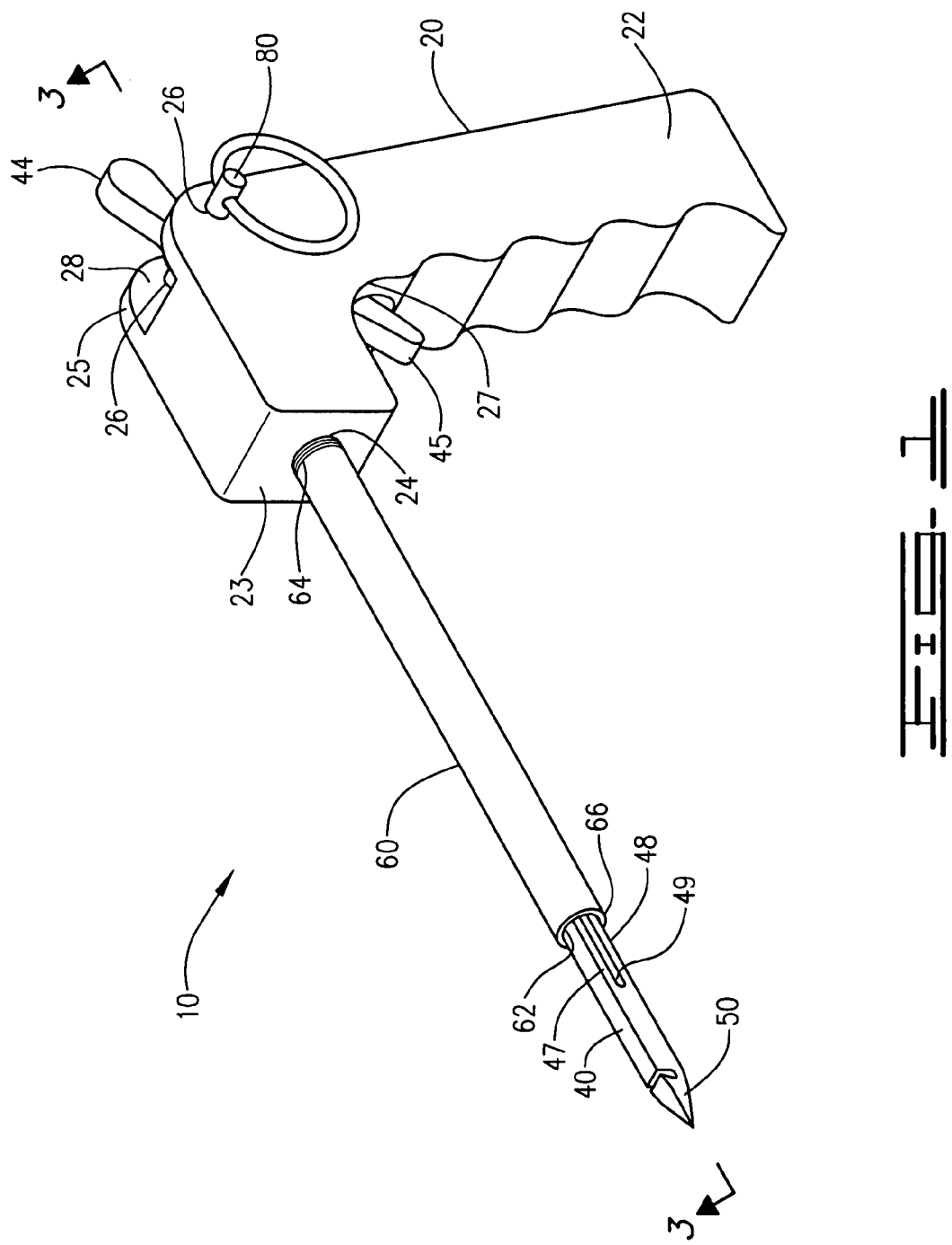
FIG. 1 is an upper perspective view of the steerable surgical instrument.

A single hand held and operational surgical instrument having a steerable, bi-directionally active capability is disclosed allowing a surgeon to insert the operation end 50 or instrument tip through soft tissue in a non-linear pathway, reducing the amount of damage to collateral tissues during the course of the surgical procedure. The instrument may be presented in any number of embodiments having a variety of surgical penetrating instruments formed or attached to an operational end of the instrument, but for purposes of the present disclosed embodiment, the operational end 50 is a suture passer instrument.

Thus, the steerable surgical instrument 10, as represented and illustrated in FIGS. 1-7B of the drawings, defines a simple assembly of four components, including a handle 20, a resilient transactional member 40, an extension tube 60 and lock pin 80 which may be readily joined and assembled and disassembled for application and for cleaning, with the transactional member 40 being presented as a disposable, reusable and/or replaceable component. The handle 20, extension tube 60 and the lock pin 80 are preferably composed of a rigid metallic material which can withstand repeated use, sterilization and reassembly with little or no wear over time. The resilient transactional member 40 is made of a resilient composition selected from a plastic, nylon or other polymeric material that can be cast or molded at a low expense for a disposable embodiment with the physical character to be used for the intended use as a surgical instrument or as a reusable embodiment where is can be sterilized without affecting the quality of the component materials, such sterilization including a steam cleansing, autoclave or chemical bath without deformation of the transactional member structures.

Figure 2:
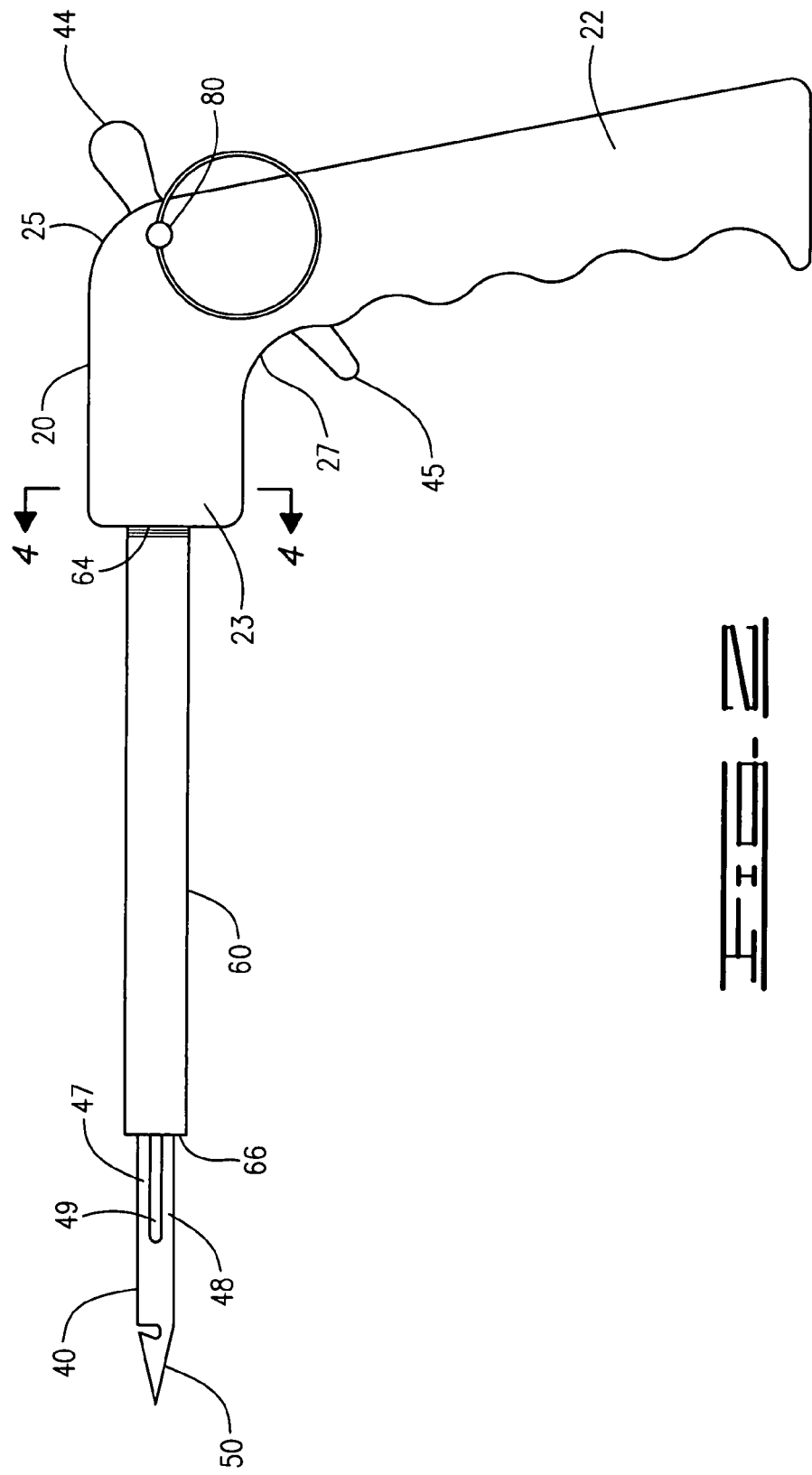
FIG. 2 is a side view of the assembled steerable surgical instrument.
Figure 3:
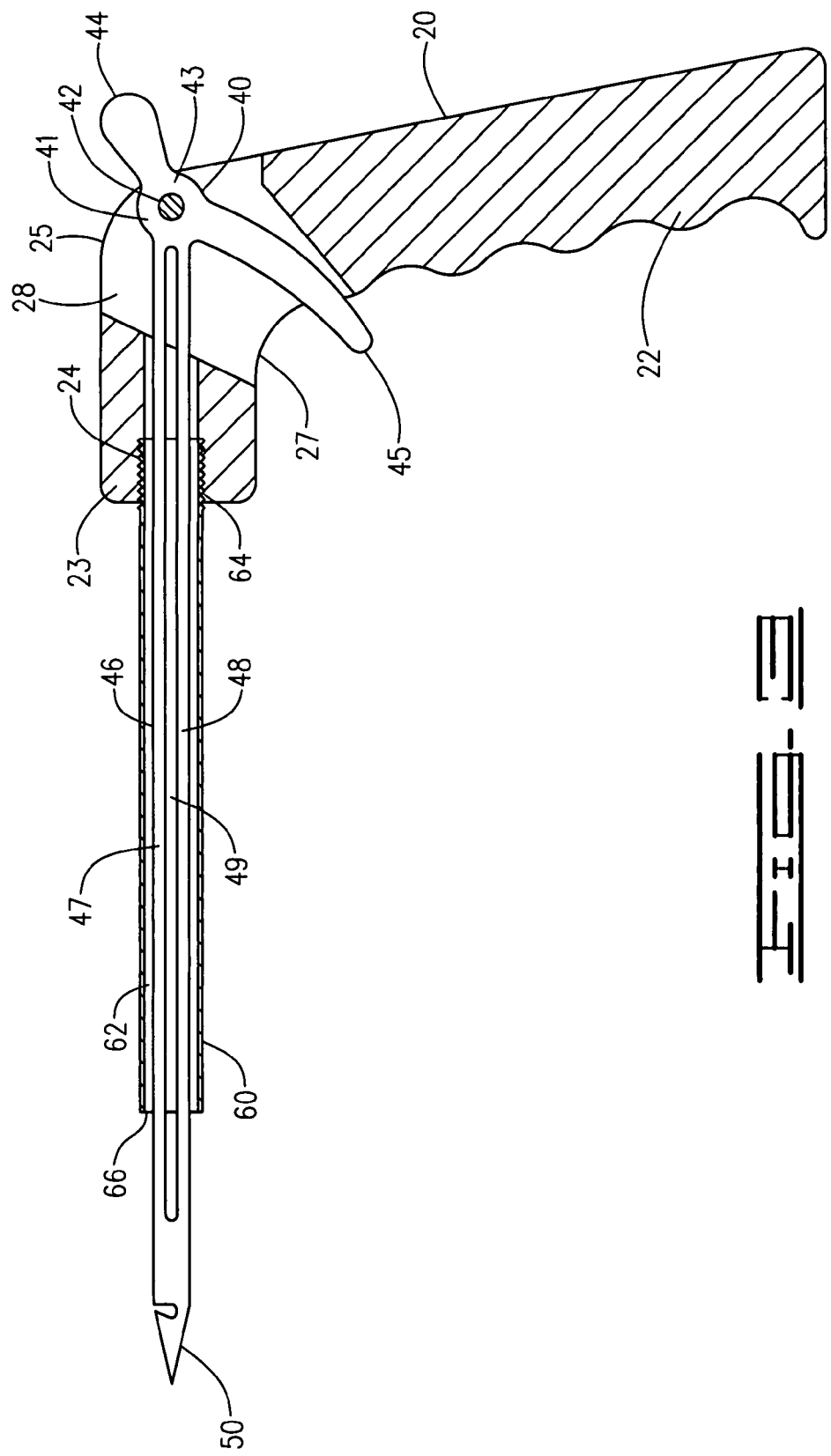
FIG. 3 is a side cross-sectional view of the steerable surgical instrument along section lines 3/3 of FIG. 1.
Figure 7A:
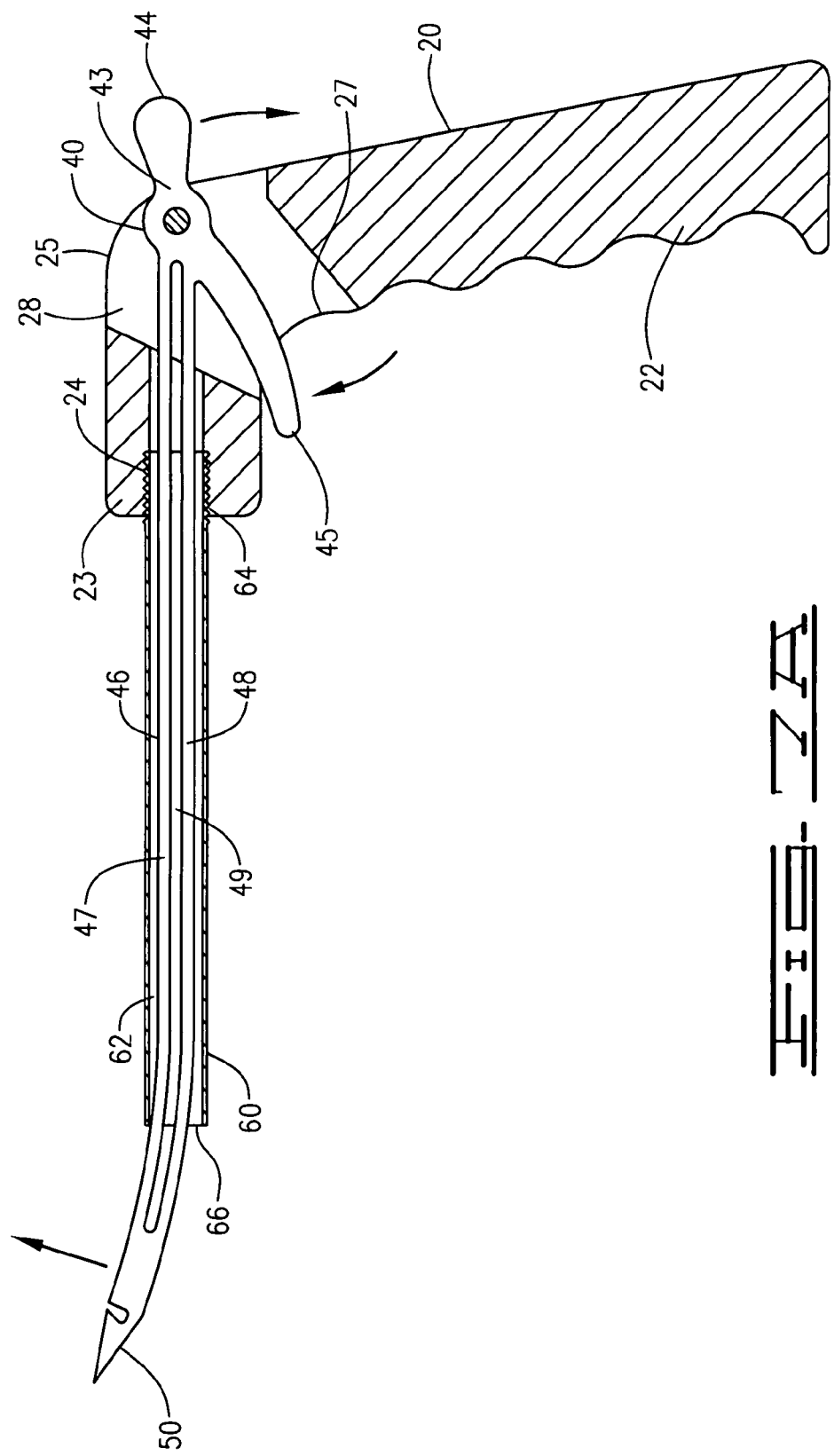
FIG. 7A is the same view as shown in FIG. 4, with the upper thumb trigger pulled downward and/or the lower finger trigger pushed forward, rotating the hub clockwise and further drawing the upper tension strut towards the trigger and the thrusting the lower tension strut forward causing the operation tip to be diverted upward.

As further defined in FIG. 6, the handle 20 further defines a lower grip portion 22, a front portion 23 including a threaded extension tube socket 24, a rear transitional angle 25 including a pair of axially aligned pin apertures 26, a front transitional angle 27 and a diagonal support housing 28 extending from the rear transitional angle 25 to the front transitional angle 27, most clearly shown in FIGS. 3, 7A and 7B. The extension tube 60 further comprises a threaded connecting end 64 which is secured within the threaded extension tube socket 24 of the handle 20, an operational end opening 66 and a longitudinal bore 62 extending from the threaded connecting end 64 to the operational end opening 66, FIG. 6. The lock pin 80 is a simple straight shaft pin which is inserted through the axially aligned pin apertures 26 to retain the steerable suture instrument together when in use, FIGS. 1, 2 and 6. The choice material for the handle 20, extension tube 60 and lock pin 80 would be stainless steel or other hard and smooth surfaced materials that can be thoroughly sterilized after use without affecting the quality of the material.

Figure 4:
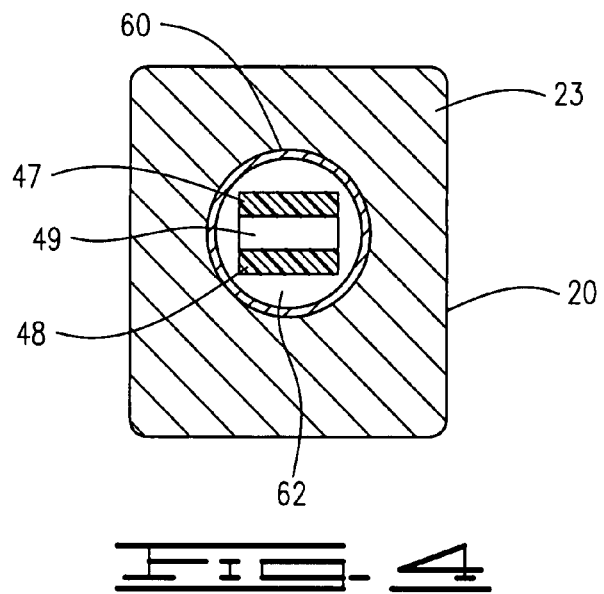
FIG. 4 is a front cross-sectional view of the steerable surgical instrument along section lines 4/4 of FIG. 2.
Figure 5:
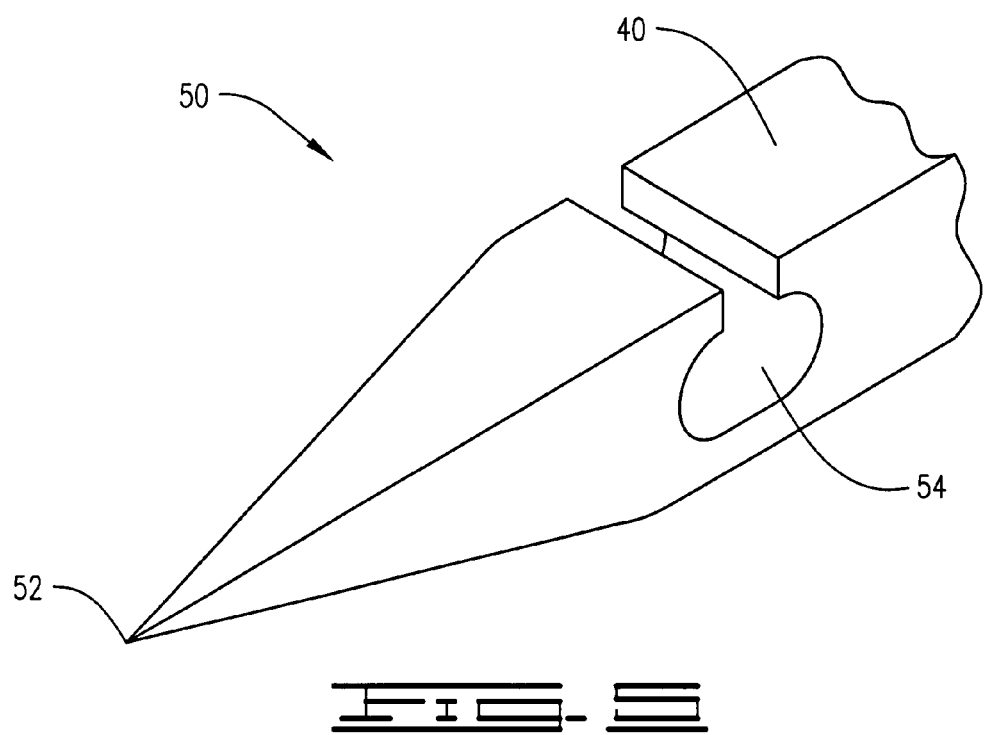
FIG. 5 is an isolated view of the operation tip of the steerable surgical instrument.

The resilient transactional member 40, FIGS. 3 and 6-7B, is an integrated single component structure further defining a hub 41 having an axial bore 42, a steering end 43 extending an upper thumb trigger 44 and a lower finger trigger 45, an intermediate strut section 46 defining an upper tension strut 47 and a lower tension strut 48 separated by a longitudinal strut slot 49, as indicated in FIG. 4 from a cross-sectional perspective, and an operational end 50. The operational end 50, in the embodiment shown in the represented embodiment of a suture passing instrument, FIG. 5, further defines a piercing tip 52 and suture insertion slot 54. As previously stated, however, this operational end 50 may be provided in other embodiments of surgical instrument devices, not shown, and the operational end 50 may comprise an attachments means allowing the attachment of a variety of operational devices which can be used during a surgical procedure and would involve manipulation, cutting or penetration of soft tissues, better served upon a steerable surgical instrument handle as disclosed.

The resilient transactional member 40 is secured within the diagonal support housing 28 of the handle 20, as shown in FIGS. 3, 6, 7A and 7B, by the insertion of lock pin 80 through the axially aligned pin apertures 26 of the handle 20 and through the axial bore 42 of the hub 41, allowing the steering end 43 to pivot within the diagonal support housing 28, both in a forward and back direction, with the resilient transactional member 40 in a relaxed position as indicated in FIGS. 1-3. The intermediate strut section 46 is inserted through the attached extension tube 60, FIG. 3, with the operational end 50 extending and exposed beyond the operational end opening 66 prior to securing the resilient transactional member 40 within the handle 20, FIG. 2.

The resilient transactional member 40 is activated by pressing the upper thumb trigger 44 forward or pulling it downward and/or by pulling the lower finger trigger 45 against the lower grip portion 22 or pushing it forward, FIGS. 7A and 7B. The movement of the resilient transactional member 40 can also occur by the contemporaneous manipulation of the upper thumb trigger 44 and lower finger trigger 45 at the same time, the most practical operation using the thumb to move the upper thumb trigger 44 and the forefinger to manipulate the lower finger trigger 45, with the other three fingers remaining in a consistent grip on the lower grip portion 22 of the handle 20 of the instrument. By moving each or both triggers, the hub 41 is rotated in a clockwise or counter-clockwise direction in relation to the axial bore 42 as shown from the left side of the instrument in FIGS. 7A and 7B. For example, the intentional bending of the operational end 50 of the instrument in an upward direction, FIG. 7A, is caused by the pulling backwards of the upper thumb trigger 44 and/or pushing forward the lower finger trigger 45. This occurs because the clockwise rotation caused by this movement of the triggers pulls back on the upper tension strut 47 and pushes forward the lower tension strut 48 within the extension tube 60, causing the operational end 50 to be bent upwards. The opposing force applied to either or both triggers rotates the hub 41 in a counterclockwise direction, FIG. 7B, thrusting the lower tension strut 48 forward and drawing back on the upper tension strut 47 within the extension tube 60, bending the operational end 50 downwards. When the triggers 44, 45 are released, the operational end 50 returns to its straight position in regards to the extension tube, as indicated in FIGS. 1-3.

It should be noted that the steerable surgical instrument 10, in addition to providing the operational end 50 in different embodiment, may also provide the extension tube 60 in differing lengths, depending upon the degree of bending desired by the surgeons. The shorter the extension tube 60, the greater degree of bending will occur to the operational end 50 of the resilient transactional member 40 and the longer the extension tube 60, the less degree of bending will occur. The length of the extension tube 60 may also affect the resistance and force required to be exerted upon the triggers 44, 45, to cause the desired bending of the operational end 50 of the resilient transactional member 40.

Disassembly of the steerable surgical instrument 10 after use requires the removal of the lock pin 80, the removal of the resilient extension member 40 from the diagonal support housing 28 of the handle 20 and the separation of the extension tube 60 from the handle 20. Upon disassembly, the components can be decontaminated, cleaned and sanitized prior to the instruments next use, with an option of replacing the resilient transactional member 40 with a new and sterile resilient transactional member 40 if the economics are in place for a less expensive replacement than the amount of time it takes to sanitize the prior used resilient transactional member 40.

While the steerable surgical instrument 10 has been particularly shown and described with reference to a preferred embodiment thereof, it will be understood by those skilled in the art that changes in form and detail may be made therein without departing from the spirit and scope of the invention.

What is claimed is:

1. A bidirectional steerable surgical instrument for use by a surgeon for the penetration and insertion through soft tissue in a non-linear pathway to reduce damage to collateral tissues during the course of the surgical procedure, said surgical instrument comprising:

a handle defining a lower grip portion, a front portion including a threaded extension tube socket, a rear transitional angle including a pair of axially aligned pin apertures, a front transitional angle and a diagonal support housing extending from said rear transitional angle through said front transitional angle;

a resilient transactional member being an integrated single component structure further defining a hub having an axial bore, a steering end extending an upper thumb trigger and a lower finger trigger, an intermediate strut section defining an upper tension strut and a lower tension strut separated by a longitudinal strut slot, and a penetrating operational end;

an extension tube defining a threaded connection end removable secured within said threaded extension tube socket of said handle, an operational end opening and a longitudinal bore extending from said threaded connection end to said operational end opening, aid longitudinal bore providing passage through which said upper tension strut and lower extension strut traverses and from which said penetrating operational end extends beyond said operational end opening; and a lock pin inserted through said axially aligned pin apertures and said axial bore of said hub to retain the resilient transactional member within said diagonal support housing in a functional assembly, said engagement of said lock pin permitting said steering end to pivot within said diagonal support housing both in a forward and back direction to raise or lower said operational end relative to said operational end opening of said extension tube.

2. The bidirectional steerable surgical instrument, as disclosed in claim 1, wherein said resilient transactional member is activated by:
   depression of said upper thumb trigger forward or pulling said upper thumb trigger downward, pulling said lower finger trigger against said lower grip portion of said handle or pushing said lower trigger forward, and/or
   contemporaneously manipulating said upper thumb trigger and said lower finger trigger, most practical conducted during an operation using a surgeon's thumb to move the upper thumb trigger and a surgeons forefinger to manipulate said lower finger trigger, with the remaining three fingers of the surgeon maintaining a consistent grasp on said lower grip portion of said handle of said instrument, said movement of said upper and or lower trigger rotating said hub in a clockwise or counter-clockwise direction relative to said axial bore.

3. The bidirectional steerable surgical instrument, as disclosed in claim 1, wherein steering of said penetrating operational end of said surgical instrument occurs in an upward direction by pulling backwards on said upper thumb trigger and/or pushing forward upon said lower finger trigger producing a directional rotation of said hub around said axial bore causing a pulling force upon said upper tension strut and a pushing force upon said lower tension strut within said extension tube while a downward direction occurs by pushing forward said upper thumb trigger and/or retracting said lower finger trigger rotates said hub in an opposing direction around said axial bore and occurring in the upward bending of said penetrating operational end, applying a pushing force upon said lower tension strut and a pulling force upon said upper tension strut within the extension tube, said penetrating operational end returning to a straight position relative to said extension tube when no force is applied to said triggers.

4. The bidirectional steerable surgical instrument, as disclosed in claim 1, wherein said operational end is a suture passer, further defining a piercing tip and suture insertion slot.

5. The bidirectional steerable surgical instrument, as disclosed in claim 1, further comprising:
   said handle, extension tube and lock pin are rigid metal products providing extended use and being subject to medical standard hygienic cleaning after use and disassembly;
   said resilient transactional member is an inexpensive integrated polymeric composition with the intent of being disposed of after a single use, with a new sterile resilient transactional member to be used upon reassembly of said surgical instrument subsequent to post-operative cleaning of said handle, extension tube and lock pin.

* * * * *